(12) United States Patent
Massey et al.

(10) Patent No.: US 11,504,055 B2
(45) Date of Patent: Nov. 22, 2022

(54) SYSTEMS AND METHODS FOR ANALYZING CUTANEOUS CONDITIONS

(71) Applicant: IKO PTE. LTD., Singapore (SG)

(72) Inventors: Jeremy Mark Massey, Singapore (SG); Syed Haroon Alam, Lahore (PK); Paul Lorenz Bigliardi, Minneapolis, MN (US); Mei Bigliardi-Qi, Minneapolis, MN (US)

(73) Assignee: IKO PTE. LTD., Singapore (SG)

( * ) Notice: Subject to any disclaimer, the term of this patent is extended or adjusted under 35 U.S.C. 154(b) by 405 days.

(21) Appl. No.: 16/639,122

(22) PCT Filed: Aug. 15, 2018

(86) PCT No.: PCT/SG2018/050414
§ 371 (c)(1),
(2) Date: Feb. 13, 2020

(87) PCT Pub. No.: WO2019/035768
PCT Pub. Date: Feb. 21, 2019

(65) Prior Publication Data
US 2020/0205723 A1    Jul. 2, 2020

(30) Foreign Application Priority Data

Aug. 17, 2017  (SG) .......................... 10201706752X

(51) Int. Cl.
*A61B 5/00* (2006.01)
*G06T 7/00* (2017.01)
*G06T 17/20* (2006.01)

(52) U.S. Cl.
CPC ............ *A61B 5/441* (2013.01); *A61B 5/0064* (2013.01); *G06T 7/0014* (2013.01); *G06T 17/20* (2013.01);
(Continued)

(58) Field of Classification Search
None
See application file for complete search history.

(56) References Cited

U.S. PATENT DOCUMENTS

| 10,007,971 B2 * | 6/2018 | Xiong ................... G06T 7/0014 |
| 2005/0033142 A1 * | 2/2005 | Madden ................. A61B 5/444 600/407 |

(Continued)

FOREIGN PATENT DOCUMENTS

| CN | 101966083 A1 | 2/2011 |
| GB | 2389500 A | 12/2003 |

OTHER PUBLICATIONS

Korotkov, Konstantin, et al. "A new total body scanning system for automatic change detection in multiple pigmented skin lesions." IEEE Transactions on Medical Imaging 34.1 (2014): 317-338.*

(Continued)

*Primary Examiner* — Ryan M Gray
(74) *Attorney, Agent, or Firm* — Fulwider Patton LLP

(57) ABSTRACT

The following disclosure discusses systems and methods of detecting and analyzing cutaneous conditions. According to one embodiment, a 2D image of the cutaneous condition and a set of 3D point clouds associated with the 2D image are captured using an image capturing device. The 2D image and the set of 3D point clouds are sent to a computing device. The computing device generates a 3D surface according to the set of 3D point clouds. Subsequently, the computing device receives a depth map for the 2D image based upon the 3D surface from another computing device such that the depth map comprises depth data for each pixel of the 2D image. The cutaneous condition may then be measured and analyzed based upon the depth map using the computing device.

13 Claims, 10 Drawing Sheets

(52) U.S. Cl.
CPC ............... *G06T 2207/10024* (2013.01); *G06T 2207/10028* (2013.01); *G06T 2207/30088* (2013.01)

(56) References Cited

U.S. PATENT DOCUMENTS

| | | | | |
|---|---|---|---|---|
| 2009/0118600 | A1* | 5/2009 | Ortiz | A61B 5/0077 |
| | | | | 600/306 |
| 2011/0218428 | A1 | 9/2011 | Westmoreland et al. | |
| 2015/0150457 | A1* | 6/2015 | Wu | G06T 7/12 |
| | | | | 600/425 |
| 2016/0058288 | A1* | 3/2016 | DeBernardis | A61B 5/0075 |
| | | | | 600/477 |
| 2017/0231550 | A1* | 8/2017 | Do | G06T 7/11 |
| | | | | 382/128 |
| 2017/0323472 | A1* | 11/2017 | Barnes | G06F 16/58 |
| 2020/0121245 | A1* | 4/2020 | Barclay | A61B 5/1072 |
| 2022/0144844 | A1* | 5/2022 | Wei | C07D 487/04 |

OTHER PUBLICATIONS

Extended European Search Report, Application No. EP 18846308.7, dated Apr. 12, 2021, 13 pages.

Murat Arikan, Reinhold Preiner and Michael Wimmer, Multi-Depth-Map Raytracing for Efficient Large-Scene Reconstruction, IEEE Transactions on Visualization and Computer Graphics, vol. 22, No. 2 (Feb. 2018).

12 Three Dimensions (Dec. 26, 2011) https://web.archive.org/web/20111226023329/https://www.whitman.edu/mathematics/multivariable/multivariable_12_three_dimensions.pdf.

Chapter 4, Coordinate Geometry in Three Dimensions (Apr. 5, 2004) https://web.archive.org/web/20040405234200/https://orcx.phys.uvic.ca/~tatum/celmechs/cfxlm4.pdf.

* cited by examiner

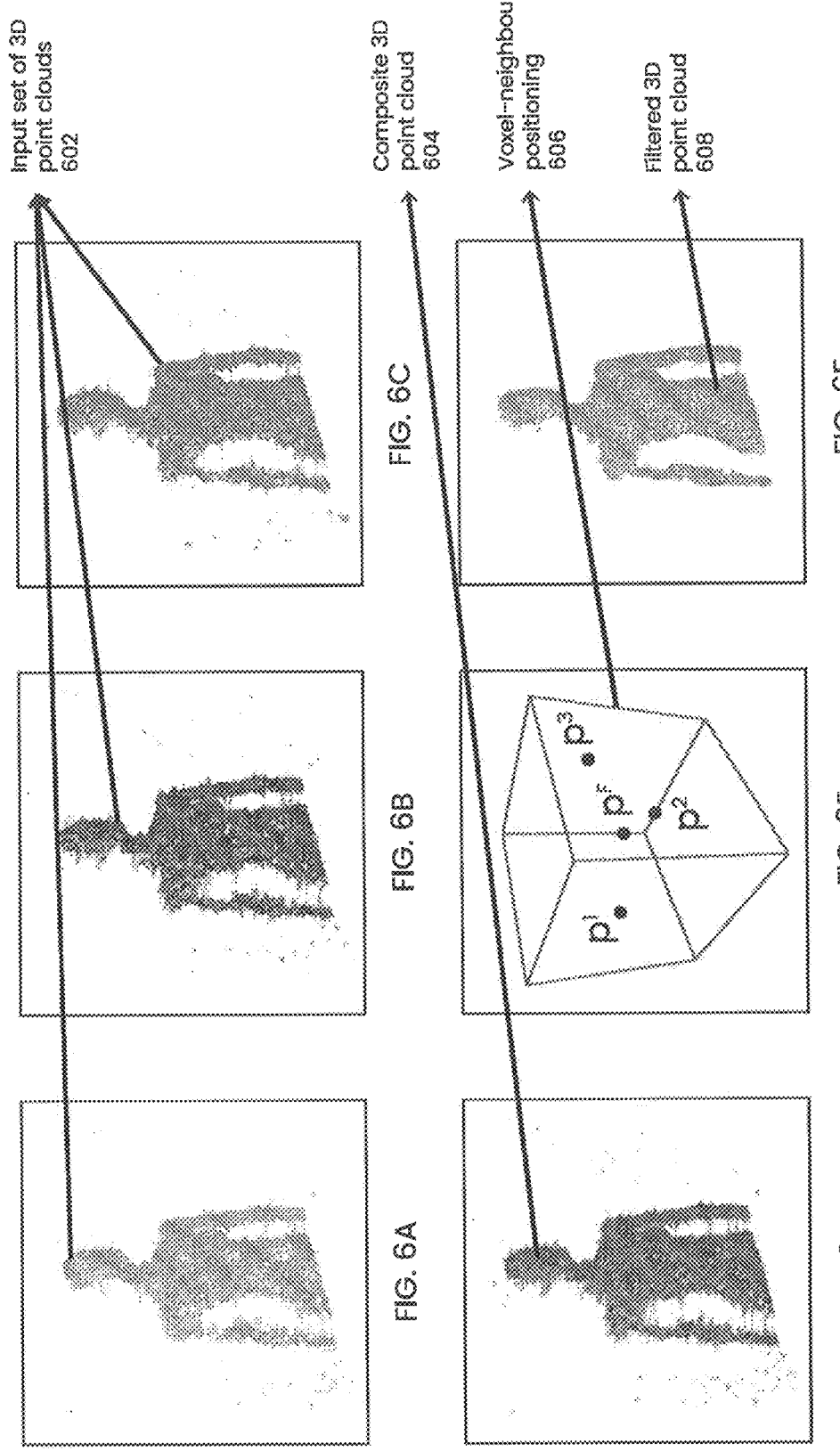

SYSTEMS AND METHODS FOR ANALYZING CUTANEOUS CONDITIONS

CROSS-REFERENCE TO RELATED APPLICATIONS

This application is the U.S. National Stage of International Application No. PCT/SG2018/050414, filed Aug. 15, 2018, which claims priority to Singapore Patent Application No. 102017067254, filed Aug. 17, 2017.

FIELD OF THE DISCLOSURE

The present disclosure relates to processing two-dimensional (2D) images in conjunction with three-dimensional (3D) data, and more particularly, to systems and methods for analyzing cutaneous conditions for diagnosis and treatment.

BACKGROUND

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

In dermatological applications, the most common method for recording and diagnosis of cutaneous conditions or conditions is to photograph the condition with a scale visible in the photograph (typically by photographing the condition alongside a ruler). This makes the image acquisition process slow and tedious. Furthermore, as there is only a single measurement reference in the photograph, surface irregularities, and camera angle variations result in low measurement accuracy.

Some systems are able to capture a complete map of a subject's skin with 2D and 3D imaging devices, but such devices are typically large, expensive, and have limited measurement options. Such devices typically rely heavily on gestalt perception and still require meticulous examination by a clinician or dermatologist.

SUMMARY

Embodiments described herein include a method for analyzing cutaneous conditions. It should be appreciated that the embodiments can be implemented in numerous ways, such as a process, an apparatus, a system, a device, or a method. Several embodiments are described below.

In one embodiment, a method of analyzing a cutaneous condition is described. The method may include an operation to receive a two-dimensional (2D) image of the cutaneous condition and a set of three-dimensional (3D) point clouds associated with the 2D image using a computing device. The method may further include an operation to generate a 3D surface according to the set of 3D point clouds using the computing device. The method may also include an operation to receive a depth map for the 2D image based on the 3D surface using the computing device such that the depth map comprises a depth value for each pixel of the 2D image. The method may include an operation to analyze the cutaneous condition based upon the 2D image and the depth map using the computing device. In an embodiment, each 3D point in each 3D point cloud in the set of 3D point clouds corresponds to at least one pixel of the 2D image.

In an embodiment, the depth map is generated using a second computing device. In an embodiment, the method may further include an operation to store the depth map in a memory device communicatively coupled to the second computing device. In an embodiment, the depth map may be calculated by implementing a ray-casting algorithm according to the 2D image and the 3D surface using the second computing device. Alternatively, the depth map may be calculated by implementing a ray-tracing algorithm according to the 2D image and the 3D surface using the second computing device.

In an embodiment, the 2D image and the set of 3D point clouds are captured using an image capturing device. In an embodiment, the method may further include an operation to revolve the image capturing device along at least one axis around a subject with the cutaneous condition to capture a set of 2D images and associated sets of 3D point clouds. In another embodiment, the method may include an operation to store the 2D image and the set of 3D point-clouds in a memory device communicatively coupled to the image capturing device.

In an embodiment, the image capturing device may include a two-dimensional (2D) camera. The method may include an operation to generate a set of pixel dimensions for each pixel of the 2D image based upon the depth value of each pixel, an angle of horizontal field of view of the 2D camera, and an angle of vertical field of view of the 2D camera using the computing device. In an embodiment, the 2D camera may capture a colored 2D image of the cutaneous condition. Alternatively, the 2D camera may capture a monochromatic 2D image of the cutaneous condition. In an embodiment, the 2D camera may have a resolution of at least 8 megapixels.

In an embodiment, the image capturing device may include a three-dimensional (3D) device. In an embodiment, the 3D device may be a 3D scanner. Alternatively, the 3D device may be a 3D camera such that the 3D camera captures the set of 3D point clouds corresponding to the 2D image.

In an embodiment, the 3D surface may be an interpolated 3D surface mesh. In an embodiment, the 3D surface may depict contours of the cutaneous condition. In an embodiment, the 3D surface may be generated by filtering out a set of aberrations in at least one 3D point cloud in the set of 3D point clouds using the computing device. In an embodiment, the 3D surface may be generated by using at least one interpolation algorithm using the computing device.

In an embodiment, analyzing the cutaneous condition may further include an operation to measure a size of the cutaneous condition using the computing device.

In an embodiment, analyzing the cutaneous condition may further include an operation to determine a variance in the size of the cutaneous condition using the computing device.

In an embodiment, analyzing the cutaneous condition may further include an operation to automatically diagnose the cutaneous condition according to the variance in the size of the cutaneous condition using the second computing device.

In an embodiment, a system for analyzing a cutaneous condition is disclosed. The system may include an image capturing device that captures a two-dimensional (2D) image of the cutaneous condition and a set of three-dimensional (3D) point clouds associated with the 2D image. The system may further include a computing device communicatively coupled to the image capturing device and a second computing device such that the computing device may receive the 2D image and the set of 3D point clouds from the image capturing device. The computing device may also generate a 3D surface according to the set of 3D point clouds. The computing device may further receive a depth map for the 2D image based on the 3D surface from the second computing device such that the depth map comprises depth data for each pixel of the 2D image. The computing device may analyze the cutaneous condition based on the depth map.

In an embodiment, the image capturing device may further include a 2D camera such that the 2D camera captures the 2D image. In an embodiment, image capturing device may further include a 3D device such that the 3D device captures the set of 3D point clouds. In an embodiment, the image capturing device may further include a battery such that the battery powers the image capturing device. Similarly, the image capturing device may also include a flash apparatus such that the flash apparatus includes at least one light-emitting diode. The image capturing device may further include a touchscreen display.

In an embodiment, the system may include at least one storage device communicatively coupled with at least one of the second computing device and the computing device such that the storage device stores the depth map. In an embodiment, at least one storage device comprises at least one of a group consisting: an internal hard drive, an external hard drive, an Universal Serial Bus (USB) drive, a solid state drive, and a network-attached storage device.

In an embodiment, the computing device and second computing device may include at least one of a group consisting of microprocessors, application specific integrated circuits (ASICs), field programmable gate arrays (FPGAs), and advanced reduced instruction set computing machines (ARMs).

In an embodiment, the computing device is communicatively coupled to the image capturing device and the second computing device via at least one network connection. In an embodiment, the network connection may be a Wi-Fi, Bluetooth, Ethernet, fiber optic connection, infrared, Near Field Communication, or co-axial cable connection.

In an embodiment a system for automatically detecting a cutaneous condition is disclosed. The system may include an image capturing device that automatically captures a set of two-dimensional (2D) images of a subject and a set of three-dimensional (3D) point clouds associated with each 2D image in the set of 2D images. The system may also include a computing device communicatively coupled to the image capturing device and a second computing device such that the computing device automatically receives the set of 2D images of the subject and the set of 3D point clouds for each 2D image. The computing device may also automatically generate a 3D rendition of the subject based on the set of 3D point clouds. Further, the computing device may automatically receive a depth map for each 2D image in the set of 2D images from the second computing device such that the depth map comprises depth data for each pixel of each 2D image. The system may include a storage device communicatively coupled to the computing device such that the storage device automatically stores the depth map.

In an embodiment, the client server may further include an analysis module such that the analysis module may automatically generate measurements of the cutaneous condition based on the depth map and the 2D image. The computing device may also automatically determine a variance in the cutaneous condition based on comparing the measurements condition with previously stored measurements of the cutaneous condition. The computing device may automatically generate a diagnosis recommendation according to the variance in the cutaneous conditions.

BRIEF DESCRIPTION OF DRAWINGS

In the drawings:

FIGS. 6A, 6B, 6C, 6D, 6E, and 6F illustrate exemplary steps for filtering data noise in a set of point clouds according to an embodiment of the present invention;

DETAILED DESCRIPTION OF THE DRAWINGS

Figure 1:
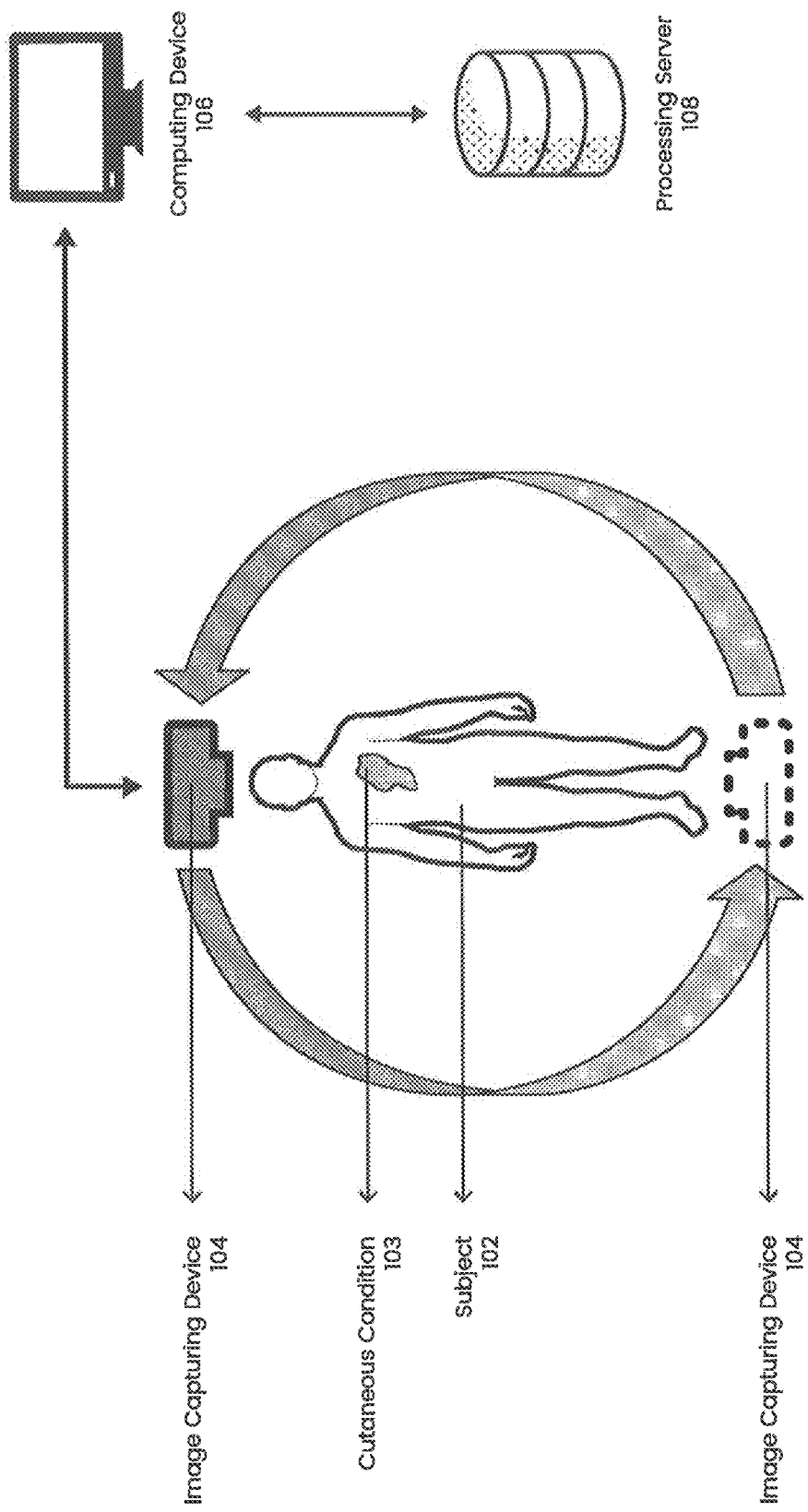
FIG. 1 illustrates an exemplary system for analyzing cutaneous conditions in accordance with an embodiment of the present invention.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments of the present invention relate to integrated circuits. The integrated circuits may be any suitable type of integrated circuit, such as microprocessors, application-specific integrated circuits, digital signal processors, memory circuits, or other integrated circuits. If desired, the integrated circuits may be programmable integrated circuits that contain programmable logic circuitry. In the following description, the terms 'circuitry' and 'circuit' are used interchangeably.

In the drawings, specific arrangements or orderings of schematic elements, such as those representing devices, modules, instruction blocks and data elements, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship or association between or among two or more other schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships or associations between elements. For example, where a connecting element represents a communication of signals, data or instructions, it should be understood by those skilled in the art that such element may represent one or multiple signal paths (e.g., a bus), as may be needed, to affect the communication.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in the specification.

The following disclosure discusses systems and methods for detecting and analyzing cutaneous conditions. In one embodiment, a method of analyzing a cutaneous condition is described. A 2D image of the cutaneous condition and a set of 3D point clouds associated with the 2D image are captured using an image capturing device. The 2D image and the set of 3D point clouds are sent to a computing device. The computing device generates a 3D surface according to the set of 3D point clouds. The 3D surface is sent to a second computing device. Subsequently, the second computing device calculates a depth map for the 2D image based upon the 3D surface such that the depth map comprises depth data for each pixel of the 2D image. The cutaneous condition may then be measured and analyzed based upon the depth map.

As used herein, "cutaneous conditions" or "cutaneous features" refer to any medical or cosmetic conditions or responses (such as allergy test or exposure responses) that affect the integumentary system i.e. the organ system that encloses the body and includes skin, hair, nails, mucous membranes, and related muscles, fat, glands and gland activity (such as sweat and sebum) and conditions such as dry skin, greasy skin, skin temperature and symptoms such as macules, papules, nodules, vesicles, blisters, pustules, abscess, infection, inflammation, hives, crusts, desquamation, erosions, ulcers, atrophy, hypertrophy, poikilodermy, lichenification, moles (including melanoma and skin cancer), reactions to tests (such as allergy tests, diagnostic or trials) or other exposures associated with said medical or cosmetic conditions. Conditions of the human integumentary system constitute a broad spectrum of diseases, also known as dermatoses, as well as many non-pathologic states. Clinically, the diagnosis of any particular skin condition is made by gathering pertinent information regarding the presenting skin lesion(s), including the location (such as arms, head, legs), symptoms (pruritus, pain), duration (acute or chronic), arrangement (solitary, generalized, annular, linear), morphology (macules, papules, vesicles), and color (red, blue, brown, black, white, yellow).

In the following disclosures, terms "voxel," "volumetric pixel" and "3D pixel" may be used interchangeably. As used herein "voxel" or "volume element" refers to a value on a regular grid in three-dimensional space. As with pixels in a bitmap, voxels themselves do not typically have their position, that is their coordinates, explicitly encoded along with their values. Instead, the position of a voxel is inferred based upon its position relative to other voxels that is a voxel's position in the data structure that makes up a single volumetric space. In an embodiment, the voxels may be based on different models, for example, gridded voxel model, sparse voxel model, or octree voxel model.

FIG. 1 illustrates an exemplary system for analyzing cutaneous conditions in accordance with an embodiment of the present invention. Referring now to FIG. 1, computing device 106 receives 2D images and related 3D point clouds of cutaneous condition 103 afflicting subject 102 from image capturing device 104 and additional data from processing server 108.

In an embodiment, subject 102 is a human being afflicted with a dermatological condition, for example melanoma, that presents itself in the form of cutaneous condition 103, for example cancerous moles or lesions. In an embodiment, subject 102 may be an animal, plant, or other living specimen. In still another embodiment, subject 102 may be a mannequin, cadaver (human or otherwise), or any other object that may be used for testing purposes. In an embodiment, cutaneous condition 103 may be a mole, lesion, cut, abrasion, boil, or some other condition affecting one or more layer of subject's skin, hair or nails. In an embodiment, subject 102 lies prone on a platform. In another embodiment, subject 102 stands on a platform. The platform may be an examining table, metal platform, gurney, bed, or any other structure of various shapes and sizes and made from different materials that is capable of supporting the weight of subject 102. In an embodiment, the platform may be mechanized or motorized i.e. the platform may be adjusted to alter the height (from the ground or floor on which the platform is resting), orientation, angle of inclination (with respect to the ground or floor on which the platform is resting). The motorized platform may also be capable of rotating.

In an embodiment, image capturing device 104 revolves around subject 102 to capture one or more 2D images and related 3D point clouds of cutaneous condition 103. In an embodiment, image capturing device 104 is connected to a dolly mounted on rails that is attached to the platform and image capturing device 104 revolves around subject 102 along a fixed path. Similarly, image capturing device 104 may capture 2D images and 3D points of cutaneous condition 103 by being manually revolved around subject 102. In an embodiment, image capturing device 104 is revolved around subject 102 by a robot that is controlled by a user. In an embodiment, the robot may be controlled remotely. In another embodiment, the robot may be automatically controlled and manipulated by computing device 106 to reduce time to capture a set of 2D images and associated 3D point clouds. In an embodiment, image capturing device 104 may be communicatively coupled to computing device 106 via Wi-Fi, Bluetooth, Near Field Communication (NFC), Ethernet cable, fiber optic cable, or some other means of transmitting data.

In an embodiment, computing device 106 is similar to computer system 300 described in relation to FIG. 3 below.

In an embodiment, computing device 106 may be communicatively coupled to a second computing device. The second computing device may perform some computationally intensive tasks and transmit the results to computing device 106. In an embodiment, the two computing devices may be configured as a client and server system, such that the computing device 106 is the client device and the other computing device is processing server 108. In an embodiment, processing server 108 is similar to computer system 300 described in relation to FIG. 3 below. In an embodiment, processing server 108 may be a cloud-based server for processing images and related 3D point clouds or 3D surfaces or other 2D image related data. In an embodiment, computing device 106 and processing server 108 may be one or more special-purpose computing devices that implement the techniques described herein. The special-purpose computing devices may be hard-wired to perform the techniques, or may include digital electronic devices such as one or more application-specific integrated circuits (ASICs), field programmable gate arrays (FPGAs), or other programmable logic devices (PLDs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 2:
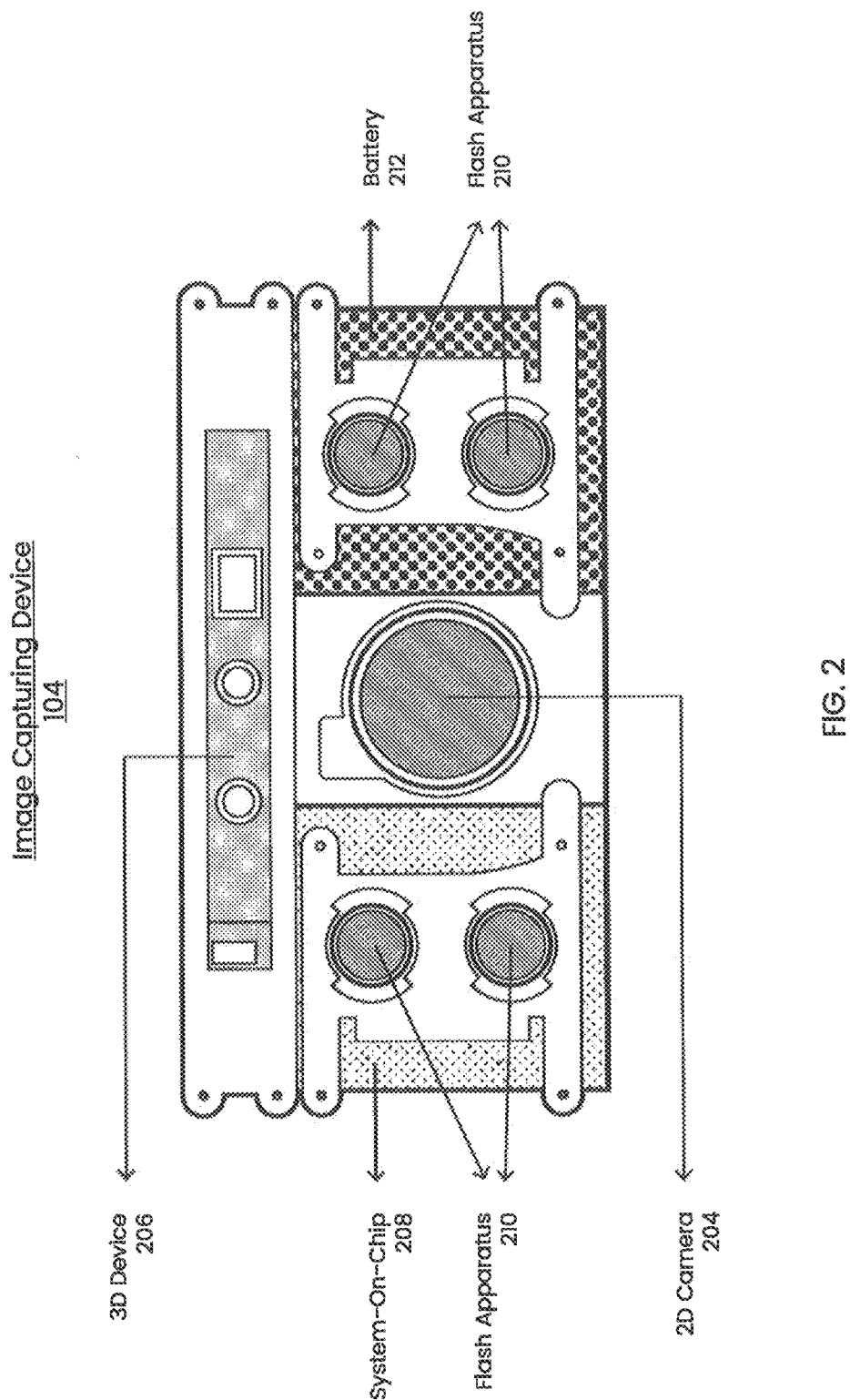
FIG. 2 illustrates an exemplary image capturing device in accordance with an embodiment of the present invention.

FIG. 2 illustrates an exemplary image capturing device in accordance with an embodiment of the present invention. Referring now to FIG. 2, image capturing device 104 may incorporate 2D camera 204 communicatively coupled to 3D device 206. 2D camera 204 and 3D device 206 may share flash apparatus 210. Image capturing device 104 may be powered by battery 212 and controlled or operated by system-on-chip 208.

In an embodiment, 2D camera 204 is a high-resolution 2D color camera. In an embodiment, 2D camera 204 is a digital camera. For example, 2D camera 204 maybe a compact camera, a smartphone camera, mirrorless camera, a Digital Single Lens Reflex camera, an Electronic Viewfinder, Interchangeable Lenses camera, or a medium format camera. In an embodiment, 2D camera 204 may have a resolution between eight and two hundred megapixels. In an embodiment, 2D camera 204 may have more than one lens. For example, 2D camera 204 may have one lens for capturing color pictures and one lens for capturing monochromatic pictures, which are then stitched together by system-on-chip 208. In another embodiment, 2D camera 204 may be an analog camera. For example, 2D camera 204 may be a film camera or large format camera.

In an embodiment, 2D camera 204 is communicatively coupled to 3D device 206. 3D device 206 may be a structured light depth camera utilizing infrared projection for 3D point cloud generation. 3D device 206 may be a non-contact 3D scanner. For example, 3D device 206 may be a time-of-flight 3D laser scanner, a triangulation based 3D scanner, a modulated light 3D scanner, or a volumetric 3D scanner.

In an embodiment, 2D camera 204 and 3D device 206 are communicatively coupled to system-on-chip 208. System-on-chip 208 may be one or more special-purpose computing devices as described above. In an embodiment, system-on-chip 208 may include a microcontroller, microprocessor, system controller, graphics processor, memory, digital signal processor, and other integrated circuit components. In an embodiment, system-on-chip 208 may be similar to computer system 300 described below in relation to FIG. 3. In an embodiment, system-on-chip 208 is utilized for real-time processing of images and data captured by image capturing device 104. In an embodiment, system-on-chip 208 implements an operating environment and a user interface to process and respond to feedback received from users of image capturing device 104.

In an embodiment, battery 212 powers image capturing device 104. Battery 212 may be a secondary or rechargeable battery. For example, battery 212 is a lithium-ion battery, lithium-polymer battery, or nickel-cadmium battery. In an embodiment, battery 212 is a primary or non-rechargeable battery. For example, battery 212 may be an alkaline battery, or a zinc carbon battery. Battery 212 allows a user to capture the set of 2D images and the set of 3D point clouds wirelessly.

In an embodiment, flash apparatus 210 is used to illuminate cutaneous condition 103. In an embodiment, flash apparatus 210 is an array of LED light connected to system-on-chip 208 on image capturing device 104. In another embodiment, flash apparatus 210 is communicatively coupled to but distinct from image capturing device 104. For example, flash apparatus 210 may include one or more flashbulb, electronic flash apparatus, high-speed flash device, or air-gap flash device. In an embodiment, flash apparatus 210 is also used to illuminate cutaneous condition 103 during acquisition of 3D point clouds. In an embodiment, image capturing device 104 may also include a touch screen display that may be used for user control, input, and feedback. The touch screen display may be a capacitive touch screen or a resistive touch screen. In an embodiment, image capturing device 104 includes a memory storage device for storing 2D images and 3D point clouds related to cutaneous condition 103. The memory storage device may be a flash storage device or a non-volatile storage device, for example a secure digital (SD) card.

Figure 3:
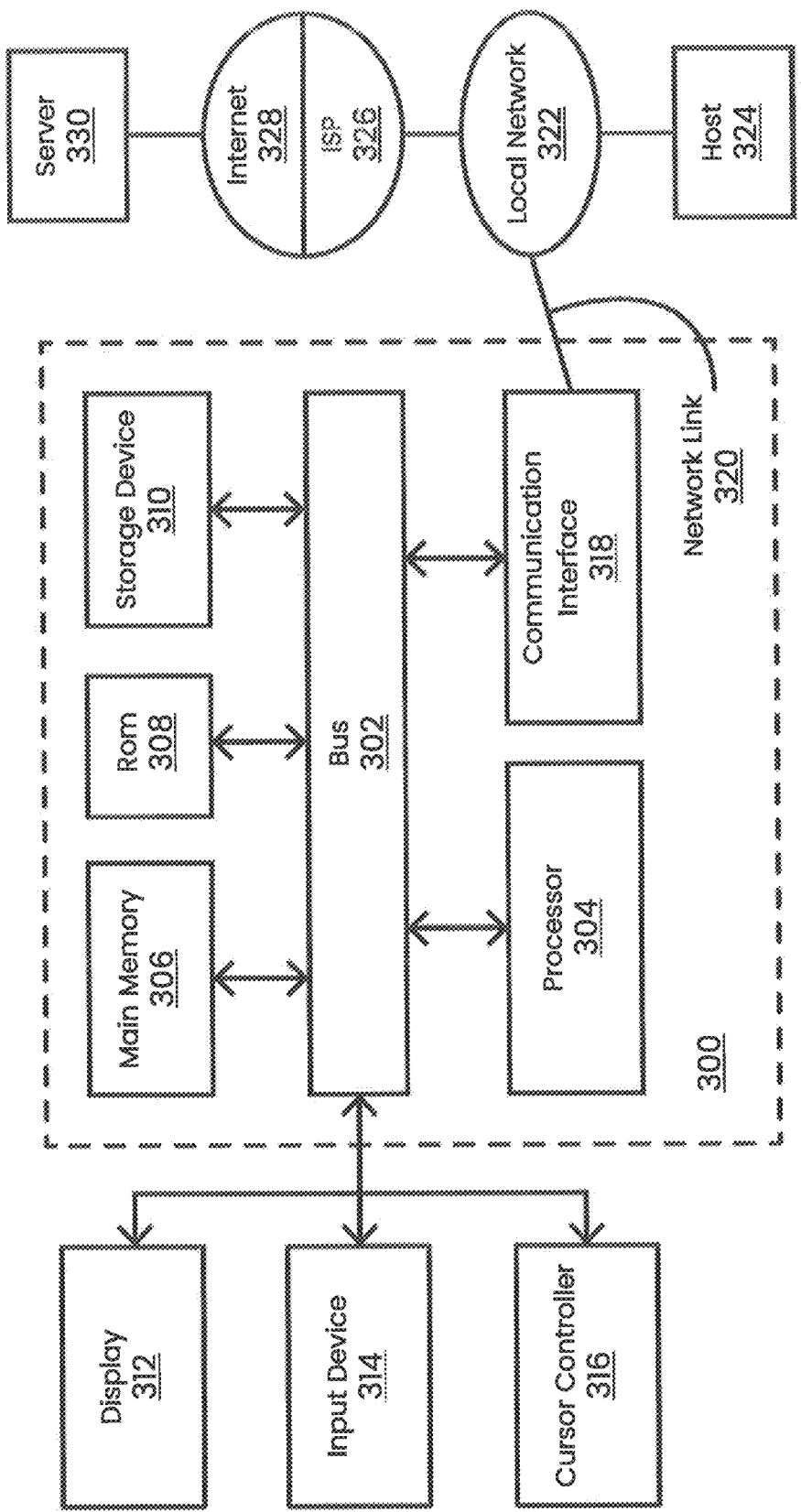
FIG. 3 illustrates an exemplary computer system in accordance with an embodiment of the present invention.

FIG. 3 illustrates a computer system 300 upon which an embodiment of the invention may be implemented. Computer system 300 includes a bus 302 or other communication mechanism for communicating information, and a hardware processor 304 coupled with bus 302 for processing information. Hardware processor 304 may be, for example, a general-purpose microprocessor.

Computer system 300 also includes a main memory 306, such as a random access memory (RAM) or other dynamic storage device, coupled to bus 302 for storing information and instructions to be executed by processor 304. Main memory 306 also may be used for storing temporary variables or other intermediate information during execution of instructions to be executed by processor 304. Such instructions, when stored in non-transitory storage media accessible to processor 304, render computer system 300 into a special-purpose machine that is customized to perform the operations specified in the instructions.

Computer system 300 may include a bus 302 or other communication mechanism for communicating information, and a hardware processor 304 coupled with bus 302 for processing information. Hardware processor 304 may be, for example, a general-purpose microprocessor.

Computer system 300 also includes a main memory 306, such as a random-access memory (RAM) or other dynamic storage device, coupled to bus 302 for storing information and instructions to be executed by processor 304. Main memory 306 also may be used for storing temporary variables or other intermediate information during execution of instructions to be executed by processor 304. Such instructions, when stored in non-transitory storage media accessible to processor 304, render computer system 300 into a special-purpose machine that is customized to perform the operations specified in the instructions.

Computer system 300 further includes a read only memory (ROM) 308 or other static storage device coupled to bus 302 for storing static information and instructions for processor 304. A storage device 310, such as a magnetic disk, optical disk, or solid-state drive is provided and coupled to bus 302 for storing information and instructions.

Computer system 300 may be coupled via bus 302 to a display 312, such as a cathode ray tube (CRT), a liquid crystal display (LCD), plasma display, light emitting diode (LED) display, or an organic light emitting diode (OLED) display for displaying information to a computer user. An input device 314, including alphanumeric and other keys, is coupled to bus 302 for communicating information and command selections to processor 304. Another type of user input device is cursor controller 316, such as a mouse, a trackball, a touch-enabled display, or cursor direction keys for communicating direction information and command selections to processor 304 and for controlling cursor movement on display 312. This input device typically has two degrees of freedom in two axes, a first axis (e.g., x) and a second axis (e.g., y), that allows the device to specify positions in a plane.

According to one embodiment, the techniques herein are performed by computer system 300 in response to processor 304 executing one or more sequences of one or more instructions contained in main memory 306. Such instructions may be read into main memory 306 from another storage medium, such as storage device 310. Execution of the sequences of instructions contained in main memory 306 causes processor 304 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 310. Volatile media includes dynamic memory, such as main memory 306. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NV-RAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 302. Transmission media can also take the form of acoustic or light waves, such as those generated during radio-wave and infra-red data communications.

Various forms of media may be involved in carrying one or more sequences of one or more instructions to processor 304 for execution. For example, the instructions may initially be carried on a magnetic disk or solid-state drive of a remote computer. The remote computer can load the instructions into its dynamic memory and send the instructions over a telephone line using a modem. A modem local to computer system 300 can receive the data on the telephone line and use an infrared transmitter to convert the data to an infrared signal. An infrared detector can receive the data carried in the infrared signal and appropriate circuitry can place the data on bus 302. Bus 302 carries the data to main memory 306, from which processor 304 retrieves and executes the instructions. The instructions received by main memory 306 may optionally be stored on storage device 310 either before or after execution by processor 304.

Computer system 300 also includes a communication interface 318 coupled to bus 302. Communication interface 318 provides a two-way data communication coupling to a network link 320 that is connected to a local network 322. For example, communication interface 318 may be an integrated services digital network (ISDN) card, cable modem, satellite modem, or a modem to provide a data communication connection to a corresponding type of telephone line. As another example, communication interface 318 may be a local area network (LAN) card to provide a data communication connection to a compatible LAN. Wireless links may also be implemented. In any such implementation, communication interface 318 sends and receives electrical, electromagnetic or optical signals that carry digital data streams representing various types of information. For example, wireless links may be implemented through use of networking technologies like WiFi, Bluetooth, infrared, and Near-Field Communication (NFC) among others.

Network link 320 typically provides data communication through one or more networks to other data devices. For example, network link 320 may provide a connection through local network 322 to a host computer 324 or to data equipment operated by an Internet Service Provider (ISP) 326. ISP 326 in turn provides data communication services through the world wide packet data communication network now commonly referred to as the "Internet" 328. Local network 322 and Internet 328 both use electrical, electromagnetic or optical signals that carry digital data streams. The signals through the various networks and the signals on network link 320 and through communication interface 318, which carry the digital data to and from computer system 300, are example forms of transmission media.

Computer system 300 can send messages and receive data, including program code, through the network(s), network link 320 and communication interface 318. In the Internet example, a server 330 might transmit a requested code for an application program through Internet 328, ISP 326, local network 322 and communication interface 318.

Processor 304 may execute the received code as it is received, and/or stored in storage device 310, or other non-volatile storage for later execution.

Figure 4:
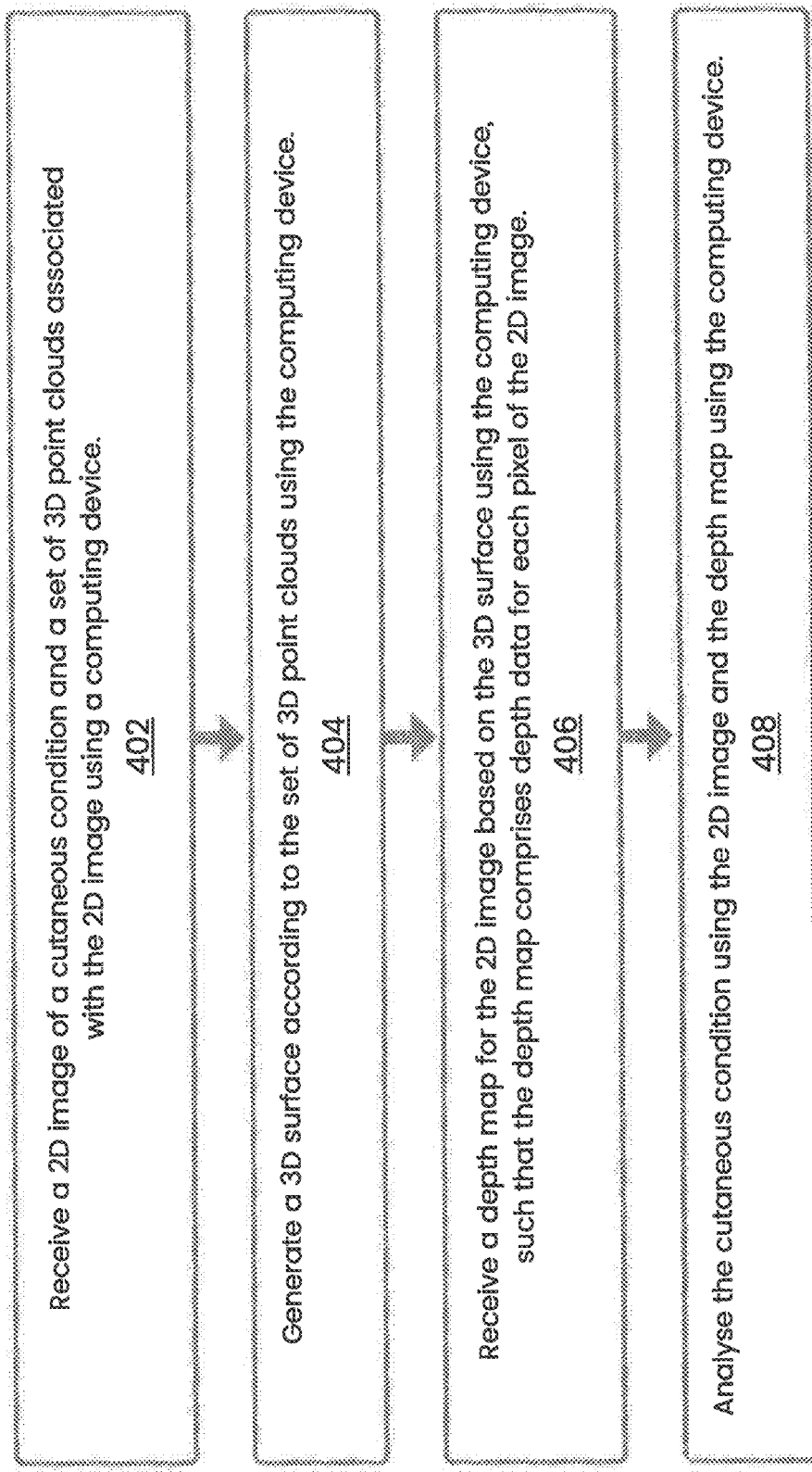
FIG. 4 illustrates an exemplary method for analyzing cutaneous conditions in accordance with an embodiment of the present invention.

FIG. 4 illustrates an exemplary method for analyzing cutaneous conditions in accordance with an embodiment of the present invention. For the purposes of illustrating clear examples, FIG. 4 will be discussed in relation to FIG. 1, FIG. 2, and FIG. 3.

Referring now to FIG. 4, at block 402, computing device 106 receives a 2D image of cutaneous condition 103 and a set of 3D point clouds associated with the 2D image. In an embodiment, the 2D image and the set of 3D point clouds is captured by image capturing device 104. In an embodiment, each 3D point in each 3D point cloud in the set of 3D point clouds corresponds to at least one pixel of the 2D image. In an embodiment, when a capture is triggered by image capturing device 104, 2D camera captures and stores a 2D color image on image capturing device 104 using system-on-chip 208.

In an embodiment, 3D device 206 captures and stores multiple 3D point clouds on image capturing device 104 during a capture event. Ideally, each point cloud may be composed of as many points as there are pixels in the corresponding 2D image. However, in practice, only points corresponding to certain pixels are captured due to limitations in depth imaging methods caused by sensor resolution constraints, projector resolution limitations and optics. In an embodiment, 3D device 206 acquires multiple point clouds for each individual capture event to eliminate noise in the data by comparing the differences in the multiple point clouds. In an embodiment, the operating frequency of 3D device 206 is determined by system-on-chip 208. For example, 3D device 206 may operate at a nominal frequency of sixty hertz to capture a number of point clouds with minimal time interval to minimize potential misalignment caused by movement of image capturing device 104 during the data acquisition process while still providing enough data for noise filtering.

In an embodiment, the image capturing device 104 sends the set of 2D images and the set of 3D point clouds to computing device 106. In an embodiment, the 2D images and 3D point clouds are sent over a high-speed wired or wireless network connection, for example a Wi-Fi, an Ethernet, or a fiber optic connection. In an embodiment, image capturing device 104 encrypts the set of 2D images and the set of 3D point clouds and transmits the encrypted set of 2D images and the set of 3D point clouds to computing device 106 over a secure communication channel. For example, image capturing device 104 may encrypt the set of 2D images and the set of 3D point clouds using a cryptographic hash function. In an embodiment, image capturing device 104 may compress the sets of 2D images and 3D point clouds before sending them to computing device 106. The compressed sets of 2D images and 3D point clouds may reduce the resources, for example time, bandwidth, and processing cycles, to transmit the data to computing device 106. Image capturing device 104 may use lossy or lossless data compression techniques and compression standards, for example Moving Picture Experts Group (MPEG) 1,2,4 or High Efficiency Video Coding (HEVC) H.261, H.262, H.264, H.265, Joint Photographic Expert Group (JPEG) Portable Network Graphics (PNG), Multiple-Image Network Graphics (MNG), or Tagged Image File Formats (TIFF).

At step 404, computing device 106 generates a 3D surface from the set of 3D point clouds. In an embodiment, computing device 106 performs 3D point cloud filtering prior to generating the 3D surface. The point cloud filtering process is further discussed below in reference to FIGS. 6A-6F. In an embodiment, the 3D surface is a high-resolution triangulated 3D mesh comprising a set of triangles that are connected by their common edges or corners derived from the filtered 3D point cloud data. In an embodiment, the 3D surface is an interpolated 3D mesh.

At step 406, computing device 106 receives a depth map for the 2D image based on the 3D surface such that that the depth map comprises depth data for each pixel of the 2D image. In an embodiment, computing device 106 generates the depth map. In an embodiment, the interpolated 3D mesh generated in step 404 is then used for ray-casting to produce per-pixel depth data for each pixel of the 2D image. As used herein, "ray-casting" refers to computer graphics algorithms that use the geometric algorithm of ray tracing. The idea behind ray casting is to trace rays from the camera, one per pixel, and find the closest surface blocking the path of that ray. In an embodiment, the per-pixel depth data also accounts for the resolution and known camera properties of image capturing device 104 or 2D camera 204. In another embodiment, computing device 106 offloads the generating of depth map to processing server 108 and receives the depth map from processing server 108 via communication interface 318 and network link 320 described above in relation to FIG. 3. In an embodiment, the 3D surface generated at step 404 is transmitted to processing server 108. Processing server 108 then implements a ray-casting algorithm to generate per-pixel depth data for each pixel of the 2D image. The per-pixel data is then transmitted to computing device 106. In an embodiment, processing server 108 generates per pixel depth data for each 2D image captured during each capture event.

At step 408, cutaneous condition 103 is analyzed by computing device 106 based on the depth map. In another embodiment, cutaneous condition 103 may also be analyzed by processing server 108. In an embodiment, current measurements of cutaneous condition 103 may be compared to older measurements of cutaneous condition 103 stored by computing device 106 or processing server 108 for diagnosis purposes. For example, if cutaneous condition 103 is a lesion that was earlier measured to be two centimeters across and currently measures four centimeters across then a clinician may suspect that cutaneous condition 103 that is present on subject 102 is spreading and may require further diagnostic investigation. In an embodiment, computing device 106 or processing server 108 automatically generates suggestions based on comparing current and previously stored measurements of cutaneous condition 103. In an embodiment, computing device 106 or the processing server may store the depth maps in storage devices similar to storage device 310 described above in relation to FIG. 3.

In an embodiment, processing server 108 may combine the 3D surface generated for each 2D image for each capture event to generate a 3D surface depicting some portion of the body of subject 102. In an embodiment, processing server 108 may be calibrated to detect certain cutaneous conditions automatically. For example, processing server 108 may automatically detect moles of a size greater than five millimeters and correcting the image region of the 2D image that contains the detected mole based on camera and surface angle which provides a clean plate for image analysis.

In an embodiment, processing server 108 may generate a malignancy score for each cutaneous condition based on pre-programmed criteria. For example, some of the pre-programmed criteria may include: asymmetry of cutaneous condition 103 relative to a particular axis, borders of cutaneous condition 103 that may indicate irregular growth, number, variety, and variance in color of cutaneous condition 103, diameter of cutaneous condition 103, elevation of cutaneous condition 103 above the dermal surface, and evolution of cutaneous condition 103 over time. Persons skilled in the art would appreciate that the list of pre-programmed criteria may be expanded or further defined based on evolving medical understanding regarding cutaneous conditions and indicators of malignancy.

In an embodiment, processing sever 108 generates a combined malignancy score for subject 102 based on the malignancy scores for the various cutaneous conditions. In an embodiment, the various malignancy scores and the combined malignancy score is transmitted by the processing server 108 to computing device 106 for further analysis by a clinician. In an embodiment, processing server 108 compares current various malignancy scores and combined malignancy scores with previously stored various malignancy scores and combined malignancy scores.

Figure 5C:
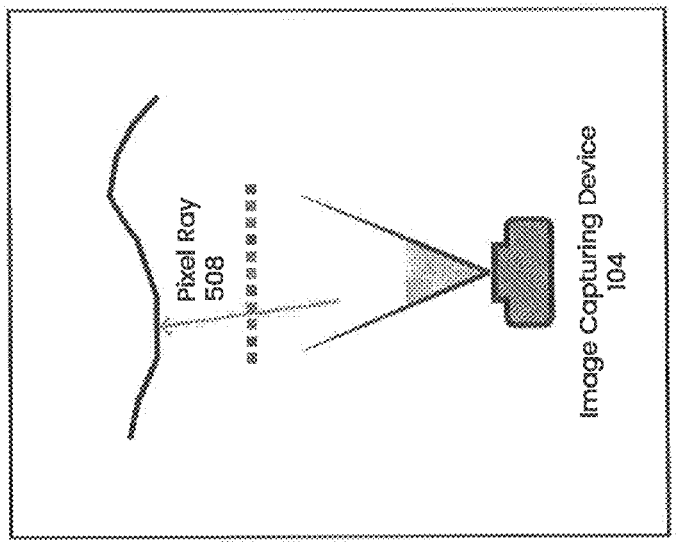
FIGS. 5A, 5B, and 5C illustrate a top-down view of exemplary steps for generating per-pixel depth data in accordance with an embodiment of the present invention.
Figure 5B:
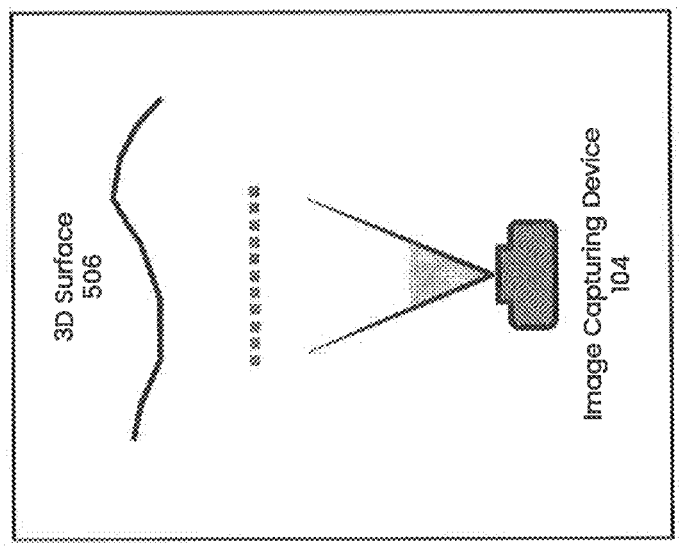
Figure 5A:
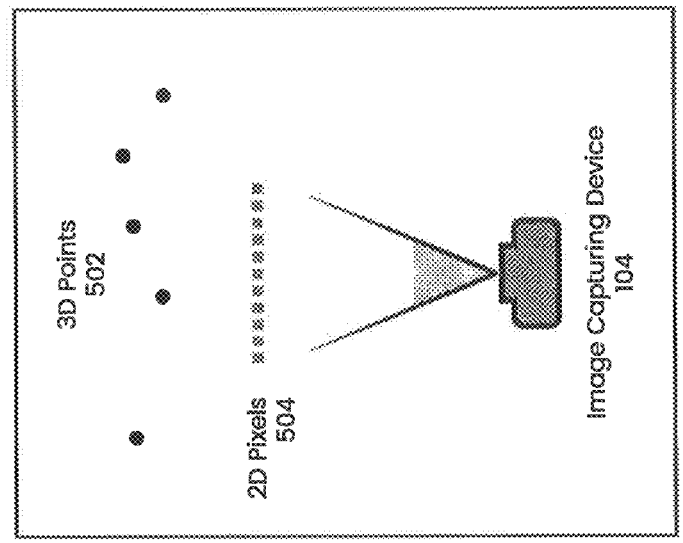

FIGS. 5A, 5B, and 5C illustrate a top-down view of exemplary steps for generating per-pixel depth data in accordance with an embodiment of the present invention. For the purposes of illustrating clear examples, FIGS. 5A, 5B, and 5C will be discussed in relation to FIGS. 1-4.

Referring now to FIG. 5A, in an embodiment, image capturing device 104 captures and stores a 2D image along with related 3D point cloud of subject 102 afflicted with cutaneous condition 103. In an embodiment, the 2D image is composed of 2D pixels 504 and 3D point cloud is composed of 3D points 502. In an embodiment, image capturing device 104 stores a set of 3D point clouds associated with the 2D image before submitting it to computing device 106 for processing at a later stage.

Referring now to FIG. 5B, in an embodiment, computing device 106 utilizes 3D points 502 of the 3D point cloud to generate a 3D surface 506. In an embodiment, 3D surface 506 is an interpolated 3D surface mesh of subject 102. In an embodiment, computing device 106 filters the set of point clouds composed of 3D points 502 prior to generating 3D surface 506 as described in FIGS. 6A, 6B, 6C, 6D, and 6E below. In an embodiment, computing device 106 utilizes a variety of interpolation techniques to produce a smooth surface geometry corresponding to surface geometry of subject 102.

For example, computing device 106 may utilize the spline method to interpolate 3D surface 506 by estimating grid cell values by fitting a minimum-curvature surface to the 3D points 502. Similarly, Inverse Distance Weighted (IDW) method for interpolating 3D surfaces estimates cell values by averaging the values of nearby 3D points 502. The closer a 3D point is to the center of the cell being estimated, the more weight the 3D point is given. Another interpolation technique that may be utilized by computing device 106 is the natural neighbor technique. This technique uses a weighted average of neighboring 3D points and creates 3D surface 506 that does not exceed the minimum or maximum values in the 3D point clouds. Still another interpolation technique is the kriging technique. Kriging technique involves forming weights from surrounding measured values to predict values at unmeasured locations. Persons skilled in the art will appreciate that the disclosed invention can be implemented in conjunction with a wide variety of techniques for interpolating 3D surface 506.

Referring now to FIG. 5C, in an embodiment, computing device 106 calculates the distance of points on the 3D surface 506 corresponding to each pixel of pixels 504 of 2D image as observed from the point-of-view of image capturing device 104. In an embodiment, computing device 106 transmits 3D surface 506 to processing server 108 and processing server 108 utilizes various techniques to calculate the distance of points on the 3D surface 506 corresponding to each pixel of pixels 504 of 2D image as observed from the point-of-view of image capturing device 104. In an embodiment, computing device 106 or processing server 108 utilize ray-casting techniques to calculate the distance for pixels 502.

In an embodiment, computing device 106 traces a ray for each pixel of 2D image such that the ray originates from a simulated image capturing device and passes through the pixel. The ray may then intersect 3D surface 506 and yield a depth measurement for the pixel. In an embodiment, computing device 106 utilizes ray-tracing algorithm to generate depth data for each pixel of 2D image. Persons skilled in the art will appreciate that the above-described methods of calculating depth data are not limiting. Other surface intersection and distance measurement techniques may be used. In an embodiment, the per-pixel depth data generated by computing device 106 by application of ray-casting techniques may be stored in a data structure. For example, the data structure may be an array or a list. Persons skilled in the art would appreciate that the per-pixel depth data corresponds to actual distance values. Actual distance values based on measurement units (for example meters or inches) so a value of 0.63728 would correspond to 0.63728 meters, or 63.728 cm. The actual distance values do not require further decoding or interpolation. In an embodiment, the per-pixel depth data may be used by computing device 106 or processing server 108 for further measurement, detection, and analysis of cutaneous conditions.

FIGS. 6A, 6B, 6C, 6D, 6E, and 6F illustrate an exemplary method of filtering data noise in a set of point clouds according to an embodiment of the present invention. For the purposes of formulating clear examples, FIGS. 6A, 6B, 6C, 6D, 6E, and 6F will be discussed with reference to FIG. 1-5.

FIGS. 6A, 6B, and 6C depict input set of 3D point clouds 602 that may be captured by 3D device 206 of image capturing device 104. In an embodiment, each point cloud in the set of clouds is related to one capture event and one or more pixels of a 2D image captured by 2D camera 204.

In an embodiment, input set of 3D point clouds 602 is than subject to noise-removal mechanisms that utilize voxel-based neighbor checking similar to the natural neighbor technique and point position averaging similar to IDW as described above in relation to FIGS. 5A-5C.

Referring now to FIG. 6D, in an embodiment, computing device 106 combines input set of point clouds 602 to generate composite 3D point cloud 604. In an embodiment, composite 3D point cloud 604 is generated based on comparing the variation across regions of input set of point clouds 602 using voxel-based cloud division across the bounds of input set of point clouds 602.

Referring now to FIGS. 6E and 6F, in an embodiment, computing device 106 generates filtered 3D point cloud 608 by utilizing voxel-neighbor positioning 606 technique. For example, for each voxel, a point is required to be present from a minimum number of point clouds before the points in the voxel are determined to be valid and an average of their positions is used for that region. This eliminates 3D points that maybe considered data noise, as noise typically only exists in individual clouds and probabilistically unlikely to persist across all the point clouds in input set of point clouds 602. In an embodiment, computing device 106 may perform additional filtering on filtered 3D point cloud 608 to remove outlier segments, smooth small noise not removed in the multi-frame noise removal and structure the 3D point data in a manner better suited for triangulation. For example, some techniques to perform additional filtering may include plane fit point normal estimation, simplification, and bi-lateral filtering.

Figures 7A, 7B, 7C:
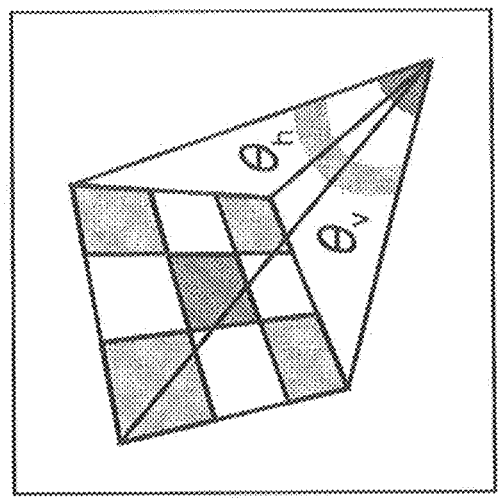
FIGS. 7A, 7B, and 7C illustrate exemplary steps for generating device-space position of a pixel of a 2D image in accordance with an embodiment of the present invention.

FIGS. 7A, 7B, and 7C illustrate exemplary steps for generating device-space position of a pixel of 2D image in accordance with an embodiment of the present invention. For the purposes of illustrating clear examples, FIGS. 7A-7C will be discussed in relation to FIGS. 1-4. As used herein, "device-space" refers to a 3D position in a coordinate system relative to the device such that the device has a position and orientation at the origin (0, 0, 0). For example, for FIGS. 7A-C image capturing device 104 is at the origin.

Referring now to FIGS. 7A-7C, in an embodiment, the per-pixel depth data or depth map generated by computing device 106 or processing server 108 in step 406 as described in relation to FIG. 4 may be utilized to calculate the dimensions of a given pixel in the 2D image by computing device 106 or processing server 108. The pixel dimensions of pixels capturing cutaneous condition 103 may be useful for analyzing cutaneous condition 103.

In an embodiment, the dimensions of a given pixel may be calculated according to the depth value of the given pixel and four neighboring pixels. In an embodiment, the depth values of the four neighboring pixels help to establish the actual or real-world locations of the four corners of the pixel. For example, with reference to FIG. 7A, the dimensions of pixel p may be calculated based on the depth value of the four neighboring pixels $p_1^N$, $p_2^N$, $p_3^N$, and $p_4^N$.

To calculate the device space positions of pixels p, $p_1^N$, $p_2^N$, $p_3^N$, and $p_4^N$ we first assign two-dimensional coordinates to the pixels. For example, with reference to FIG. 7B, the pixels p, $p_1^N$, $p_2^N$, $p_3^N$, and $p_4^N$ are assigned coordinates (1, 1), (0, 2), (2, 2), (0, 0), and (2, 0) respectively. Other embodiments may use other coordinates. Any arbitrary coordinates may be used as long as the same coordinate scheme is used for all pixels in 2D image.

With reference to FIG. 7C, in an embodiment, the method for calculating the dimensions of the given pixel p may further utilize the known horizontal field of view $\Theta_H$ and vertical field of view $\Theta_V$ of 2D camera 204 to calculate each pixel's camera-space position in 3-dimensions. In an embodiment, computing device 106 or processing server 108 determines the device-space position of pixels p, $p_1^N$, $p_2^N$, $p_3^N$, and $p_4^N$ based on the parameters above. In an embodiment, the device-space positions of the pixels p, $p_1^N$, $p_2^N$, $p_3^N$, and $p_4^N$ are calculated according to the formula below:

$$x = \frac{\tan \theta_H}{2} \cdot D \cdot \left(\frac{C_h \cdot 2}{R_h} - 1\right) \quad y = \frac{\tan \theta_V}{2} \cdot D \cdot \left(\frac{C_v \cdot 2}{R_v} - 1\right) \quad z = D$$

In the formula above, D represents the depth of the given pixel, C represents the coordinates of the pixel as discussed above in reference to FIG. 7B, with $C_h$ and $C_v$ representing the horizontal and vertical coordinate value respectively and R representing the resolution of the total image, with $R_h$ and $R_v$ representing the horizontal and vertical resolution respectively. $\Theta_H$ and $\Theta_V$ represent the horizontal and vertical 2D camera 204 field-of-view angles. The device-space positions thus calculated by computing device 106 for pixels p, $p_1^N$, $p_2^N$, $p_3^N$, and $p_4^N$ allows for further measurements to be made of the pixel p based on the desired area or path measurement. Persons skilled in the art will appreciate that utilizing a per-pixel evaluation allows for accurate surface feature measurement regardless of contour and camera or device angle. Furthermore, when calculating dimensions of a region encompassing multiple pixels, for example dimensions of cutaneous condition 103, the same process is used across all relevant pixels with a sum of the result of each pixel representing the result of the region being measured.

Figure 8A:
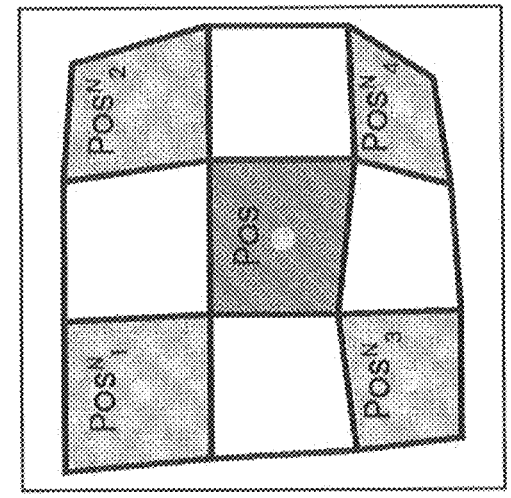
FIGS. 8A, 8B, and 8C illustrate exemplary steps for generating pixel dimensions of a pixel of a 2D image in accordance with an embodiment of the present invention.
Figure 8B:
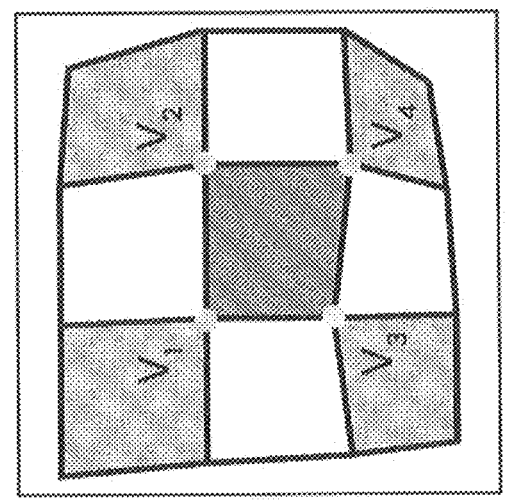
Figure 8C:
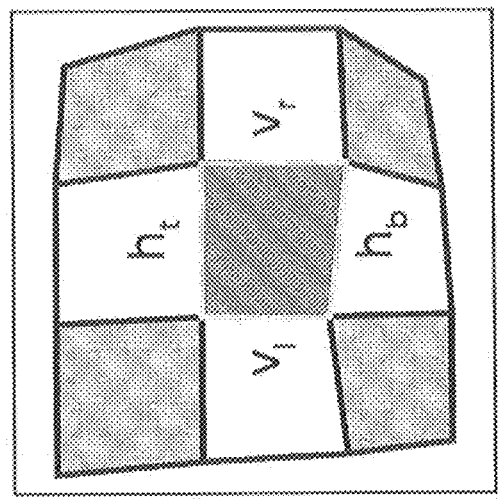

FIGS. 8A, 8B, and 8C illustrate exemplary steps for generating pixel dimensions of a pixel of a 2D image in accordance with an embodiment of the present invention. For the purposes of illustrating clear examples, FIGS. 8A-C will be discussed in relation with FIGS. 7A-7C.

Referring now to FIGS. 8A-8C, in an embodiment, computing device 106 or processing server 108 calculates the pixel dimensions of a given pixel based on the previously determined device-space position of the given pixel and its neighboring pixels in FIGS. 7A-7C. Continuing the example from above, after determining the camera-space positions of pixels p, $p_1^N$, $p_2^N$, $p_3^N$, and $p_4^N$, computing device 106 or processing server 108 may generate pixel-space corner vectors using vector subtraction. As used herein, "pixel-space" refers to a 3D position relative to the corresponding 3D position of a reference pixel such that 3D position of reference pixel is at the origin (0, 0, 0).

Furthermore, "corner vector" refers to the 3D location of each corner of the given pixel in pixel-space. With reference to FIG. 8A, Pos and $Pos_{1-4}^N$ refer to position vectors for pixels p and $p_{1-4}^N$ respectively. With reference to FIG. 8B, refer to corner vectors for given pixel p. The corner vectors are calculated according to the formula below:

$$V_n = (Pos_n^N - Pos)/2$$

Thus, if $Pos = x_0, y_0, z_0$ and $Pos_1^N = x_1, y_1, z_1$, then:

$$V_1 = (Pos_1^N - Pos)/2$$

$$V_1 = (x_1, y_1, z_1 - x_0, y_0, z_0)/2$$

$$V_1 = (x_1 - x_0)/2, (y_1 - y_0)/2, (z_1 - z_0)/2$$

Referring now to FIG. 8C, in an embodiment, computing device 106 or processing server 108 can utilize the corner vectors to calculate the horizontal and vertical dimensions of the pixel. In an embodiment, the dimensions are calculated according to the formulas below:

$$h_t^V = V_2 - V_1$$

$$h_t = \sqrt{h_t^V \cdot x_0^2 + h_t^V y_0^2 + h_t^V z_0^2}$$

$$h_b^V = V_4 - V_3$$

$$h_b = \sqrt{h_b^V \cdot x_0^2 + h_b^V y_0^2 + h_b^V z_0^2}$$

$$v_l^V = V_1 - V_3$$

$$v_l = \sqrt{v_l^V \cdot x_0^2 + v_l^V y_0^2 + v_l^V z_0^2}$$

$$v_b^V = V_2 - V_4$$

$$v_b = \sqrt{v_b^V \cdot x_0^2 + v_b^V y_0^2 + v_b^V z_0^2}$$

The corner vectors are calculated in pairs for horizontal and vertical dimensions with $h_t$ representing the top horizontal dimension, $h_b$ representing the bottom horizontal dimension, $v_l$ representing the left vertical dimension and $v_r$ representing the right vertical dimension. $x_0, y_0, z_0$ represent the position vector for the given pixel. In an embodiment, only two of the four dimensions are required for further measurement or analysis of cutaneous condition 103. For example, only the aggregated pixel width and aggregated pixel height may be required for calculating surface area of cutaneous condition 103 and computing device 106 or processing server 108 may utilize an average of corresponding edges to provide a single pixel width/height value combination.

Figure 9C:
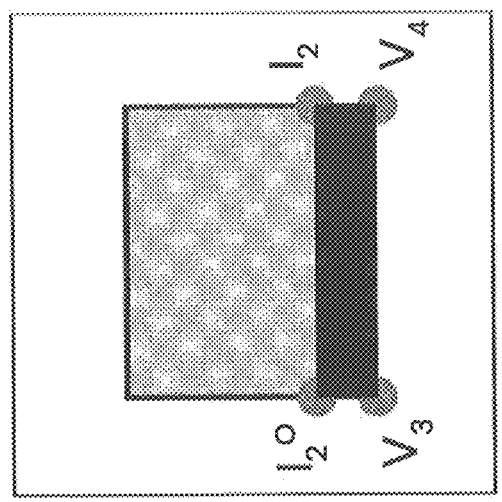
FIGS. 9A, 9B, and 9C illustrate exemplary steps for measuring sub-pixel regions of a 2D image in accordance with an embodiment of the present invention.
Figure 9B:
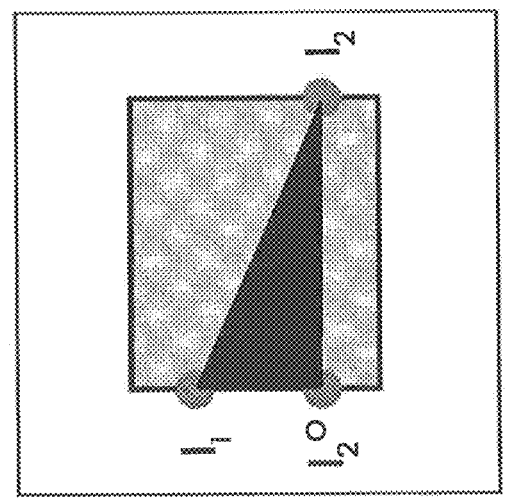
Figure 9A:
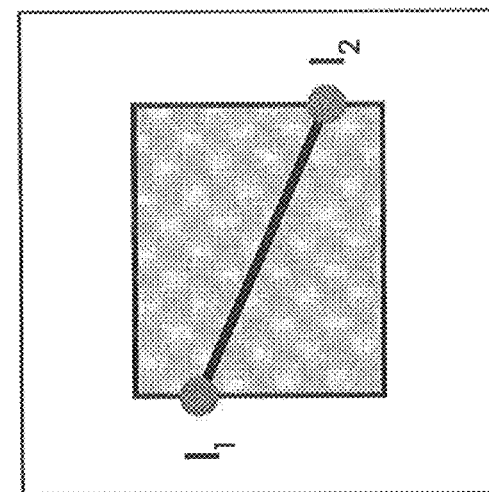

FIGS. 9A, 9B, and 9C illustrate exemplary steps for measuring sub-pixel regions of a 2D image in accordance with an embodiment of the present invention. For illustrating clear examples, FIGS. 9A-9C will be discussed with reference to previously discussed figures. The pixel dimensions of one or more pixels generated by computing device 106 or processing server 108 as described above in relation to FIGS. 8A-8C may be utilized to measure sub-pixel regions of a given pixel in the 2D image by computing device 106 or processing server 108. The sub-pixel measurements for regions of a 2D image may be useful to analyze cutaneous condition 103 where the cutaneous condition 103 is not depicted by a whole number of pixels i.e. cutaneous condition 103 is included in portions of certain pixels.

Referring now to FIGS. 9A-9C, in an embodiment, a pixel-space measurement field may represent a sub-pixel region, for example a line as depicted in FIG. 9A, or a partial pixel area for example, FIG. 9B and FIG. 9C. In an embodiment, normalized pixel edge intersections are used to deduce new camera-space vectors via linear interpolation of the corner vectors that were discussed above in relation to FIGS. 8A-8C. In an embodiment, a length is calculated by calculating the distance between a pair of intersection point vectors. For example in FIG. 9A, the two intersection point vectors $I_1$ and $I_2$ are used to determine the length of the line shown in FIG. 9A.

Similarly, when a partial area is required, the "interior" of the pixel is determined and three triangle point vectors are calculated using the opposite of the relevant edge intersection and trigonometric functions to calculate the triangle properties. For example, in FIG. 9B, the triangle formed by intersection vectors $I_2$, $I_2^O$, and $I_1$ is used to calculate the partial pixel area. In the event of an intersection triangle not representing the complete pixel "interior", a rectangle is used to calculate the remaining area dimensions if required. For example, in FIG. 9C, the rectangle formed by intersection vectors $I_2$, $I_2^O$, $V_3$, and $V_4$ is used to calculate the area of the sub-pixel region bounded by the intersection vectors.

In an embodiment, edge intersections are calculated using a standard 2D infinite line intersection formula given below with resulting intersections occurring outside of the normalized pixel space being discarded.

$$a_1 = L_1^e \cdot y - L_1^s \cdot y \quad a_2 = L_2^e \cdot y - L_2^s \cdot y$$

$$b_1 = L_1^s \cdot x - L_1^e \cdot x \quad b_2 = L_2^s \cdot x - L_2^e \cdot x$$

$$c_1 = a_1 \cdot L_1^s \cdot x + b_1 \cdot L_1^s \cdot y \quad c_2 = a_2 \cdot L_2^s \cdot x + b_2 \cdot L_2^s \cdot y$$

$$\Delta = a_1 \cdot b_2 - a_2 \cdot b_1$$

$$x = \frac{b_2 \cdot c_1 - b_1 c_2}{\Delta} \quad y = \frac{a_1 \cdot c_2 - a_2 c_1}{\Delta}$$

In the formula above, $L_1^s$ represents the line 1 start coordinates, $L_1^e$ represents the line 1 end coordinates. Similarly, $L_2^s$ represents the line 2 start coordinates, $L_2^e$ represents the line 2 end coordinates. In an embodiment, the calculations described in FIGS. 5A-5C, 6A-6F, 7A-7C, 8A-8C, and 9A-9C are carried out by a specialized computational and analysis module of computing device 106 or processing server 108.

Figure 10:
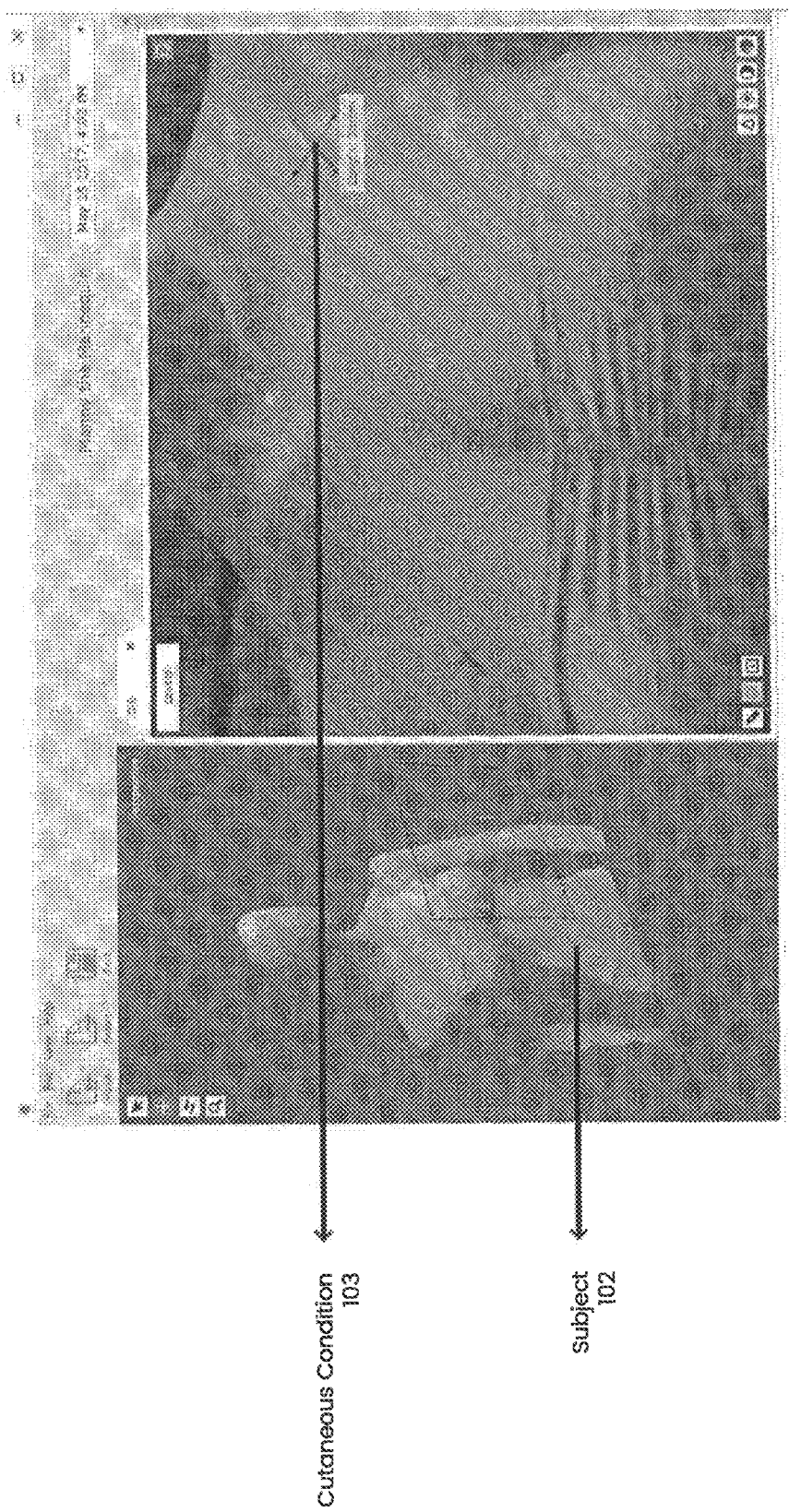
FIG. 10 illustrates an exemplary view of the output 2D image for analyzing cutaneous conditions in accordance with an embodiment of the present invention.

FIG. 10 illustrates an exemplary view of the output 2D image for analyzing cutaneous conditions in accordance with an embodiment of the present invention. For the purposes of illustrating clear examples, FIG. 10 will be discussed in relation with FIGS. 1-4.

In FIG. 10, subject 102 and at least one cutaneous condition 103 is viewable through a graphical user interface (GUI). In an embodiment, the GUI is implemented by a standalone application executing on computing device 106 or processing server 108. In an embodiment, the GUI is an extension of the user interface implemented on image capturing device 104 that may be manipulated by a user of the image capturing device 104 via a touchscreen as described above. In an embodiment, the GUI may allow a user to interact with the final 2D image of subject 102 along with the embedded depth data for each pixel of the 2D image by using input device 314 as described in reference to computer system 300 of FIG. 3. In an embodiment, the user may be able to manipulate the final 2D image of subject 102 for measurement and analysis of cutaneous condition 103. For example, the user may be able to rotate, zoom in or zoom out, change perspective, take screenshots, measure changes for cutaneous condition 103. In an embodiment, the user is able to initiate a side-by-side comparison in the GUI of the final 2D image and a previous final 2D image stored by the processing server 108. In an embodiment, the GUI allows the user to view cutaneous condition 103 at different magnifications, which is also useful in detecting other cutaneous conditions of different sizes.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims.

What is claimed is:

1. A method of analyzing a cutaneous condition comprising:

receiving from an image capturing device a two-dimensional (2D) image of the cutaneous condition and a set of three-dimensional (3D) point clouds associated with the 2D image using a computing device;

generating a 3D surface according to the set of 3D point clouds using the computing device;

generating a depth map for the 2D image based on the 3D surface using a second computing device, wherein the depth map comprises a depth value for each pixel of the 2D image; and analyzing the cutaneous condition based upon the 2D image and the depth map using the computing device;

wherein dimensions of each pixel in a desired area or path in the 2D image are calculated for the analysis;

wherein horizontal and vertical dimensions of the each pixel in the desired area or path in the 2D image are calculated using pixel-space corner vectors for each pixel in the desired area or path in the 2D image, according to the formulas below:

$$h_t^V = V_2 - V_1$$

$$h_t = \sqrt{h_t^V \cdot x_0^2 + h_t^V y_0^2 + h_t^V z_0^2}$$

$$h_b^V = V_4 - V_3$$

$$h_b = \sqrt{h_b^V \cdot x_0^2 + h_b^V y_0^2 + h_b^V z_0^2}$$

$$v_l^V = V_1 - V_3$$

$$v_l = \sqrt{v_l^V \cdot x_0^2 + v_l^V y_0^2 + v_l^V z_0^2}$$

$$v_b^V = V_2 - V_4$$

$$v_b = \sqrt{v_b^V \cdot x_0^2 + v_b^V y_0^2 + v_b^V z_0^2}$$

wherein, $V_1$, $V_2$, $V_3$, $V_4$ represent pixel-space corner vectors for a given pixel $x_0$, $y_0$, $z_0$ represent position vector of the given pixel $h_t$ represents top horizontal dimension of the given pixel
$h_b$ represents bottom horizontal dimension of the given pixel
$v_l$ represents left vertical dimension of the given pixel
$v_r$ represents right vertical dimension of the given pixel;
wherein the pixel-space corner vectors for the each pixel in the desired area or path in the 2D image are calculated using 3D camera-space position of the each pixel in the desired area or path in the 2D image according to the formula below:

$$V_n = (Pos_n^N - Pos)/2$$

wherein,
Pos represents position vector of the given pixel
$Pos_n^N$ represents position vectors of pixels located at corners of the give pixel
$V_n$ represents pixel-space corner vectors for the given pixel
n is 1, 2, 3 or 4;
wherein 3D camera-space position of the each pixel in the desired area or path in the 2D image is calculated according to the formulas below:

$$x = \frac{\tan \theta_H}{2} \cdot D \cdot \left( \frac{C_h \cdot 2}{R_h} - 1 \right)$$
$$y = \frac{\tan \theta_V}{2} \cdot D \cdot \left( \frac{C_v \cdot 2}{R_v} - 1 \right)$$
$$z = D$$

wherein,
D represents depth of the given pixel
C represents coordinates of the given pixel, and $C_h$ and $C_v$ represent horizontal and vertical coordinate value respectively
R represents resolution of total image, and $R_h$ and $R_v$ represent horizontal and vertical resolution respectively
$\Theta_H$ and $\Theta_V$ represent horizontal and vertical 2D camera field-of-view angles.

2. A system for analyzing a cutaneous condition comprising:
an image capturing device that captures a two-dimensional (2D) image of the cutaneous condition and a set of three-dimensional (3D) point clouds associated with the 2D image;
a computing device communicatively coupled to the image capturing device and a second computing device, wherein the computing device is configured to:
receive the 2D image and the set of 3D point clouds from the image capturing device;
generate a 3D surface according to the set of 3D point clouds;
generate a depth map for the 2D image based on the 3D surface using the second computing device, wherein the depth map comprises depth data for each pixel of the 2D image; and
analyze the cutaneous condition based on the depth map;
wherein dimensions of each pixel in a desired area or path in the 2D image are calculated for the analysis;
wherein horizontal and vertical dimensions of each pixel in the desired area or path in the 2D image are calculated using pixel-space corner vectors for each pixel in the desired area or path in the 2D image, according to the formulas below:

$$h_t^V = V_2 - V_1$$
$$h_t = \sqrt{h_t^V \cdot x_0^2 + h_t^V y_0^2 + h_t^V z_0^2}$$
$$h_b^V = V_4 - V_3$$
$$h_b = \sqrt{h_b^V \cdot x_0^2 + h_b^V y_0^2 + h_b^V z_0^2}$$
$$v_l^V = V_1 - V_3$$
$$v_l = \sqrt{v_l^V \cdot x_0^2 + v_l^V y_0^2 + v_l^V z_0^2}$$
$$v_b^V = V_2 - V_4$$
$$v_b = \sqrt{v_b^V \cdot x_0^2 + v_b^V y_0^2 + v_b^V z_0^2}$$

wherein,
$V_1, V_2, V_3, V_4$ represent pixel-space corner vectors for a given pixel
$x_0, y_0, z_0$ represent position vector of the given pixel
$h_t$ represents top horizontal dimension of the given pixel
$h_b$ represents bottom horizontal dimension of the given pixel
$v_l$ represents left vertical dimension of the given pixel
$v_r$ represents right vertical dimension of the given pixel;
wherein the pixel-space corner vectors for the each pixel in the desired area or path in the 2D image are calculated using 3D camera-space position of the each pixel in the desired area or path in the 2D image according to the formula below:

$$V_n = (Pos_n^N - Pos)/2$$

wherein,
Pos represents position vector of the given pixel
$Pos_n^N$ represents position vectors of pixels located at corners of the give pixel
$V_n$ represents pixel-space corner vectors for the given pixel
n is 1, 2, 3 or 4;
wherein 3D camera-space position of the each pixel in the desired area or path in the 2D image is calculated according to the formulas below:

$$x = \frac{\tan \theta_H}{2} \cdot D \cdot \left( \frac{C_h \cdot 2}{R_h} - 1 \right)$$
$$y = \frac{\tan \theta_V}{2} \cdot D \cdot \left( \frac{C_v \cdot 2}{R_v} - 1 \right)$$
$$z = D$$

wherein,
D represents depth of the given pixel
C represents coordinates of the given pixel, and $C_h$ and $C_v$ represent horizontal and vertical coordinate value respectively
R represents resolution of total image, and $R_h$ and $R_v$ represent horizontal and vertical resolution respectively
$\Theta_H$ and $\Theta_V$ represent horizontal and vertical 2D camera field-of-view angles.

3. The system as defined in claim 2, wherein each 3D point in each 3D point cloud in the set of 3D point clouds corresponds to at least one pixel of the 2D image.

4. The system as defined in claim 2, wherein the second computing device is configured to calculate the depth map by implementing a ray-casting algorithm or a ray-tracing algorithm according to the 2D image and the 3D surface.

5. The system as defined in claim 2, wherein the image capturing device is configured to capture the 2D image and the set of 3D point clouds.

6. The system as defined in claim 5 wherein the image capturing device is configured to revolve along at least one axis around a subject with the cutaneous condition to capture a set of 2D images and associated sets of 3D images.

7. The system as defined in claim 5 further comprising a memory device, communicatively coupled to the image capturing device, configured to store the 2D image and the set of 3D point clouds and store the depth map.

8. The system as defined in claim 5, wherein the image capturing device comprises a two-dimensional (2D) camera configured to:
  capture a colored 2D image of the cutaneous condition, and
  capture a monochromatic 2D image of the cutaneous condition.

9. The system as defined in claim 8, wherein the computing device is configured to generate a set of pixel dimensions for each pixel of the 2D image based upon the depth value of each pixel, an angle of horizontal field of view of the 2D camera, and an angle of vertical field of view of the 2D camera.

10. The system as defined in claim 5, wherein the image capturing device comprises a three-dimensional (3D) camera, and wherein the 3D camera captures the set of 3D point clouds corresponding to the 2D image.

11. The system as defined in claim 2, wherein the 3D surface is an interpolated 3D surface mesh, and wherein the 3D surface depicts contours of the cutaneous condition.

12. The system as defined in claim 2, wherein the computing device is configured to generate the 3D surface by filtering out a set of aberrations in at least one 3D point cloud of the set of 3D point clouds, and wherein the 3D surface is generated by using at least one interpolation algorithm using the computing device.

13. The system as defined in claim 2, wherein the computing device is configured to analyze the cutaneous condition by measuring a size of the cutaneous condition, determine a variance in the size of the cutaneous condition, and automatically diagnose the cutaneous condition according to the variance in the size of the cutaneous condition.

* * * * *